US00PP32849P2

(12) United States Plant Patent
Austin

(10) Patent No.: US PP32,849 P2
(45) Date of Patent: Mar. 2, 2021

(54) SHRUB ROSE PLANT NAMED 'AUSCROWD'

(50) Latin Name: *Rosa hybrida*
Varietal Denomination: AUScrowd

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/602,912

(22) Filed: Dec. 19, 2019

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

(56) References Cited

PUBLICATIONS https://www.rightroses.com/gabriel-oak# 'Gabriel Oak Review/ David Autin 2019'. Retrieved from the Internet on Jun. 25, 2020.(3 pages total).*
https://wwwpumpkinbeth.com/2019/05/new-david-austin-roses-2019/. Retrieved from the Internet on Jun. 25, 2020. (10 pages total).*

* cited by examiner

*Primary Examiner* — Susan McCormick Ewoldt
(74) *Attorney, Agent, or Firm* — KPPB LLP

(57) ABSTRACT

A variety of rose plant of the shrub class, named 'AUScrowd'. The 'AUScrowd' is a variety of a rose shrub having vigorous roses on a broad, rounded shrub with dark green foliage. The shrub bears large, many-petalled rosette blooms of a deep pink and outer petals of each bloom that pale slightly over time and have a strong fruity fragrance.

1 Drawing Sheet

Genus and species: The present invention relates to a new *Rosa hybrida* shrub of the market class 'English Rose'.

Variety denomination: The new plant has the varietal denomination 'AUScrowd'.

ORIGIN OF INVENTION

This invention relates to a new and distinct variety of shrub rose plant named 'AUScrowd', which was originated from the cross-pollination of the two 'unnamed' and unpatented seedlings of *Rosa hybrida.*

BACKGROUND OF THE INVENTION

The primary objective of this breeding was to produce a rose shrub that bears vigorous roses on a broad, rounded shrub with dark green foliage. The shrub bears large, many-petalled rosette blooms of a deep pink and outer petals of each bloom that pale slightly over time and have a strong fruity fragrance.

SUMMARY OF THE INVENTION

Among the features which distinguish the new variety from others presently available and commercial rose cultivars known to the inventor is the following combination of characteristics: large, many petalled blooms of deep pink, outer petals that pale over time, a strong fruity fragrance, a shapely, broad and rounded shrub having dark green foliage.

Asexual reproduction of the new variety by budding as performed in Albrighton, Britain shows that the foregoing and other distinguishing characteristics come true to form and are established and transmitted through succeeding asexual propagations. 'AUScrowd' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUScrowd' are two unnamed seedlings. The new rose may be distinguished from its seed parent, by the following combination of characteristics: the seed parent has smaller, pale pink open-cupped blooms compared to the large, deep-pink, many petalled rosettes of 'AUScrowd'. The new rose may be distinguished from its pollen parent, by the following combination of characteristics: the pollen parent has smaller, yellow open-cupped blooms, compared to the large, deep-pink, many petalled rosettes of 'AUScrowd'.

COMPARISON WITH THE CLOSEST COMMERCIALLY AVAILABLE CULTIVAR

The closest commercially available cultivar to the new variety are 'AUSpike' (U.S. Plant Pat. No. 30,924) and 'AUSvibrant' (U.S. Plant Pat. No. 20,960). Both 'AUSpike' and 'AUSvibrant' have a petallage of around 90, whereas the petallage of 'AUScrowd' is approximately 125. Also, when viewed from above, the shape of the bloom of both 'AUSpike' and 'AUSvibrant' is irregularly rounded, whereas the blooms of 'AUScrowd' are round. 'AUSpike' has a depth of bloom of 3.5 cm compared with 6 cm for 'AUScrowd'. The petals of 'AUSvibrant' have a reverse which is paler than the inner side, whereas the petal reverse on 'AUScrowd' is the same shade as the inner side.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUScrowd' specimens were made at the nursery in Albrighton, Wolverhampton, United Kingdom. The following description is of 1 year-old rose plants of the new variety grown in a garden environment in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2 cm long and 1.7 cm in diameter when the petals start to unfurl.

*Form*.—The bud form is broad based.

*Color*.—When sepals first divide, the bud color is RHS 67A (red-purple group). When half blown, the upper sides of the petals are RHS 53C (red group), and the lower sides of the petals RHS 53C (red group).

*Calyx*.—Shape: star shape, with the sepals folding back against the stems. Length: 6 cm. Diameter: 6 cm.

*Sepals*.—Arrangement: Regularly arranged. Color: Upper Surface: RHS 194B (grayed-green group). Lower Surface: RHS 143B (green group) with some RHS 184D (grayed-purple group). Length: 2.5 cm. Width: 1 cm. Shape: Lanceolate. Surface texture: Upper Surface: Downy. Lower Surface: Slightly glandular. Number: There are 2 normally appendaged sepals, and 3 unappendaged sepals with hairy edges. Sepal Extensions: Medium.

*Receptacles*.—Color: RHS 143B (yellow-green group) with some RHS 184D (grayed-purple group). Shape: Funnel. Size: Broad, about 1.2 cm long×1.4 cm wide. Surface: Smooth.

*Peduncle*.—Length: Medium, averaging about 8.5 cm. Surface: Glandular. Color: RHS 143B (yellow-green group). Strength: Strong.

Blooms:

*Size*.—Large, average open diameter is about 9.5 cm.

*Borne*.—Several together approximately 4-14 blooms having a rounded shape.

*Stems*.—Strength: Strong, average length is about 40 cm. Diameter: 6 mm.

*Form*.—When first open, bloom is cupped. Permanence of bloom: outer petals curl back.

*Flower type*.—Double.

Petalage:

*Number of petals under normal conditions*.—125.

*Color*.—The upper sides of the petals are RHS 67B (red-purple group). The reverse sides of the petals are RHS 72D (red-purple group). The base of the petals has a yellow spot RHS 13B (yellow group).

*Variegations*.—None.

*Discoloration*.—The general tonality at the end of the first day is RHS N66A (red-purple group), and at the end of the third day is RHS 67B (red-purple group).

*Fragrance*.—Strong. Character of fragrance: Fruity.

Petals:

*Texture*.—Satiny.

*Size*.—Width: 2.5 cm. Length: 3.8 cm.

*Surface*.—Smooth.

*Shape*.—Obovate.

*Margin*.—Entire.

*Apex shape*.—Rounded.

*Base shape*.—Acute.

*Form*.—Tips slightly incurved.

*Arrangement*.—Regular.

*Petaloids*.—Number: Few. Color: RHS 67B (red-purple group). Length: 0.6-1.8 cm. Width: 0.6-1.8 cm. Shape: Deformed petal. Margin: Entire.

*Persistence*.—Petals drop off cleanly before drying.

*Lastingness*.—On the plant: Fair about 5 days. As a cut flower: not tested.

Reproductive parts:

*Stamens*.—Number: approximately 195. Length: 8 mm.

*Anthers*.—Length: 3 mm. Color: RHS 14A (yellow-orange group). Arrangement: Regular around styles.

*Filaments*.—Color: RHS 12A (yellow group). Length: 4-5 mm.

*Pollen*.—Color: RHS 14A (yellow-orange group). Amount: Moderate.

*Pistils*.—Number: Approximately 100. Length: 6 mm.

*Styles*.—Color: RHS 145D (yellow-green group). Length: 5 mm.

*Stigmas*.—Color: RHS 153C (yellow-green group). Length: 1 mm.

*Hips*.—NONE Observed.

PLANT CHARACTERISTICS

Plant form: Shrub.

Plant growth: Vigorous.

Age to maturity: 2 years.

Mature plant: Height: 1.2 m. Width: 1.2 m.

Rootstock: *Rosa dumetorum* 'Laxa' for the observed plants.

Foliage:

*Number*.—Leaflets on normal mid-stem leaves is: 5 (including terminal leaflet).

*Size*.—Large, about 18 cm long×13.5 cm wide.

*Quantity*.—Normal. Number of leaves per flowering stem is: 10.

*Color*.—New foliage: Upper side: RHS 144A (yellow-green group) with RHS 183B (grayed-purple group). Lower side: RHS 143B (grayed-purple group). Old foliage: Upper side: RHS 147A (yellow-green group). Lower side: RHS 147B (yellow-green group).

Leaflets:

*Size*.—About 7 cm long×4.5 cm wide.

*Shape*.—Pointed oval.

*Base shape*.—Rounded.
*Apex shape*.—Acuminate.
*Texture*.—Leathery.
*Glossiness*.—Medium.
*Edge*.—Serrated.
*Serrations*.—Single and large.
*Petiole*.—Color: RHS 181D (grayed-red group). Length: 3 cm. Width: 1.5 mm. Surface Texture: Glandular.
*Petiole rachis*.—Color: RHS 181D (grayed-red group) and RHS 143B (yellow-green group). Underside: with prickles.
*Stipules*.—Length: 2 cm, smooth. Color: RHS 147A (yellow-green group).
*Auricle*.—Shape: Lanceolate. Length: 1 cm. Width: 1.5 mm. Color: RHS 143B (yellow-green group).
*Vein color*.—Color: RHS 147A (yellow-green group).
*Venation pattern*.—Reticulate.

Wood:
*New wood*.—Color: RHS 143C (yellow-green group). Bark: Smooth but with prickles.
*Old wood*.—Color: RHS 143B (yellow-green group). Bark: Smooth but with prickles.

Branching habit:
*Number*.—9.
*Dimensions*.—Length: 80 cm. Diameter: 1 cm.

Stems:
*Mature stem*.—Length: 100 cm. Diameter: 1 cm.
*Internode distance*.—10 cm. The above measurements are all variable, depending on growing conditions in a season.
*Stem pubescence present*.—No.

Prickles:
*Quantity*.—On main canes from base: Many. Number per stem length: 12 per 20 cm. On laterals from main canes: Ordinary. Number per stem length: 10 per 10 cm.
*Form*.—Deep concave.
*Length*.—5-7 mm.
*Color when young*.—RHS 183B (grayed-purple group).
*Color when mature*.—RHS 183B (grayed-purple group).

Small prickles:
*Quantity*.—Main stalk: Many. Number per stem length 100 per 10 cm. Laterals: Many Number per stem length 100 per 10 cm.
*Color*.—When young: RHS 183B (grayed-purple group). When mature: RHS 183B (grayed-purple group).

Disease resistance:
*Powdery mildew* (*podosphaera pannosa*).—Resistant.
*Downey mildew* (*peronospora species*).—Resistant.
*Blackspot* (*diplocarpon rosae*).—Resistant.
*Rust* (*phragmidium tuberculatum*).—Resistant.

Pest Resistance: Not tested.
Winter Hardiness: Not tested.
Growing conditions: Normal garden conditions.

What is claimed is:

1. A new and distinct variety of rose plant of the shrub class, substantially as herein shown and described.

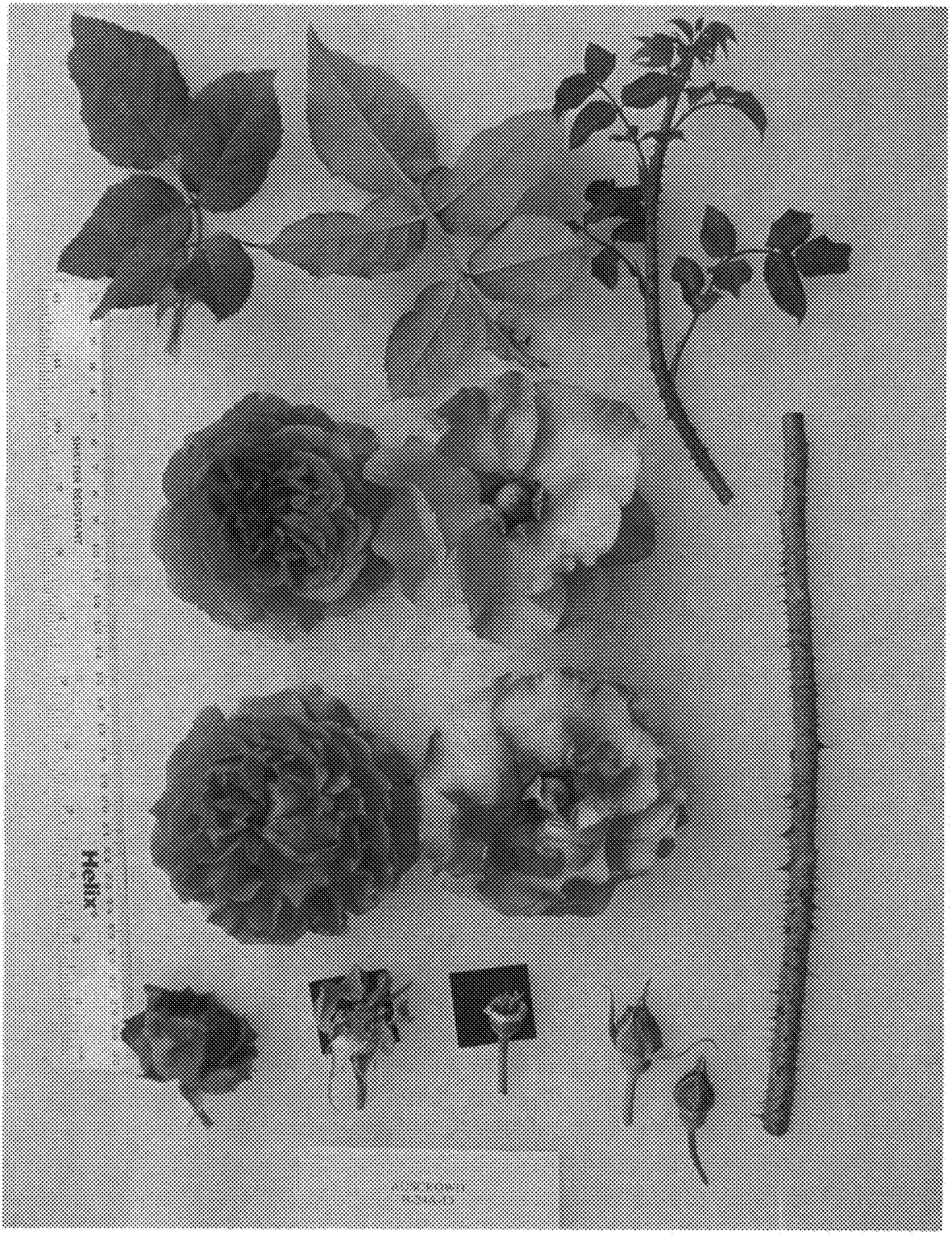

* * * * *